US00PP36762P2

(12) United States Plant Patent
Hansen

(10) Patent No.: US PP36,762 P2
(45) Date of Patent: Jun. 24, 2025

(54) ***BAPTISIA* PLANT NAMED 'Vanilla Cream II'**

(50) Latin Name: ***Baptisia* hybrid**
Varietal Denomination: Vanilla Cream II

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,303

(22) Filed: Oct. 22, 2024

(51) Int. Cl.
*A01H 6/00* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson

(57) ABSTRACT

A new and distinct plant cultivar of *Baptisia* plant named 'Vanilla Cream II' characterized by creamy-yellow flowers on long spikes beginning in late May in Michigan and continuing for about three weeks. The new plant is a winter-hardy, herbaceous perennial and produces multiple heavily-branched stems in a thick mound with tri-foliate foliage that emerges chartreuse with grey-purple blush on the margin and matures to a slight glaucous bluish-green. The new plant is suitable for landscaping as a specimen or en masse.

2 Drawing Sheets

Botanical classification: *Baptisia* hybrid.
Cultivar designation: 'Vanilla Cream II'.

STATEMENT REGARDING PRIOR DISCLOSURES UNDER 37 CFR 1.77(B)(6)

*Baptisia* 'Vanilla Cream II' was promoted with a description and photograph on a website operated by Walters Gardens, Inc. on Dec. 1, 2023, followed by the "Walters Gardens 24-25 Catalog" distributed by Walters Gardens, Inc. first on May 23, 2024. The first sale of *Baptisia* 'Vanilla Cream II' was made in private by Walters Gardens, Inc. to Hopewell. on Jun. 17, 2024. Information and plants for this sale and all sales thereafter were obtained from the inventor. No plants of *Baptisia* 'Vanilla Cream II' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Vanilla Cream II' and will be referred to hereafter by its cultivar name, 'Vanilla Cream II', and the new plant. The new plant represents a new False Indigo, a hardy herbaceous perennial grown for landscape and cut flower use.

'Vanilla Cream II' arose from an ongoing breeding program of the inventor at a wholesale perennial nursery in Zeeland, Michigan with the specific intention of improving garden worthiness of perennial false indigo plants with a wider variety of flower colors and improved garden habit.

*Baptisia* 'Vanilla Cream II' was a single seedling selection from a cross on Jun. 1, 2013, between a proprietary unreleased hybrid selection of *Baptisia cinerea* and *sphaerocarpa* (not patented) as the female or seed parent times a proprietary unreleased selection of *Baptisia alba* (not patented) as the male or pollen parent. Seeds were collected in fall of 2013 by the inventor. The seeds were sown by the inventor at a wholesale perennial nursery in Zeeland, Michigan in the fall of 2013 and the initial selection made in the spring of 2015 at the same nursery in Zeeland and given the breeder code 13-4-8 through the remaining evaluation process.

'Vanilla Cream II' was initially asexually propagated by stem cuttings at a wholesale perennial nursery in Zeeland, Michigan in 2017. The resultant plants have demonstrated that the new plant has remained stable and true to type in successive generations of asexual propagation.

The nearest comparison plants known to the inventor are: 'Vanilla Cream' U.S. Plant Pat. No. 25,663, 'Lunar Eclipse' U.S. Plant Pat. No. 25,875, 'Pink Truffles' U.S. Plant Pat. No. 26,588, 'Pink Lemonade' U.S. Plant Pat. No. 30,669, 'Ivory Towers' U.S. Plant Pat. No. 26,827, and 'Wayne's World' (not patented).

'Vanilla Cream' is shorter and more rounded in habit with shorter flowers stems that have fewer flowers. 'Lunar Eclipse' is shorter in habit and the flowers mature to light blue as they age. 'Pink Truffles' is taller in height and wider in habit and the flowers are soft pink with pale yellow keels. 'Pink Lemonade' is slightly taller and broader in habit, and the flowers open a pale yellow and mature to a dusty raspberry-purple. Both 'Ivory Towers' and 'Wayne's World' have flowers that are more white and are significantly taller in habit.

The female parent has a shorter habit and with more creamy-white flowers. The male parent has white flowers and near black peduncles.

The new plant differs from all *Baptisia* known to the inventor in the following combined traits:

1. Creamy-yellow flowers on long spikes.
2. Flowering begins in late May in Michigan and continues for about three weeks.

3. Thick mounds of multi-stemmed, heavily-branched, winter-hardy, herbaceous, habit.
4. Peduncles are near-black.
5. Tri-foliate foliage that emerges with chartreuse with a greyed-purple margin and matures to a light glaucous bluish-green.

BREF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a nine-year-old plant growing in an open full-sun trial garden in Zeeland, Michigan.

DETAILED BOTANICAL DESCRIPTION OF THE PLANT

Figure 1:
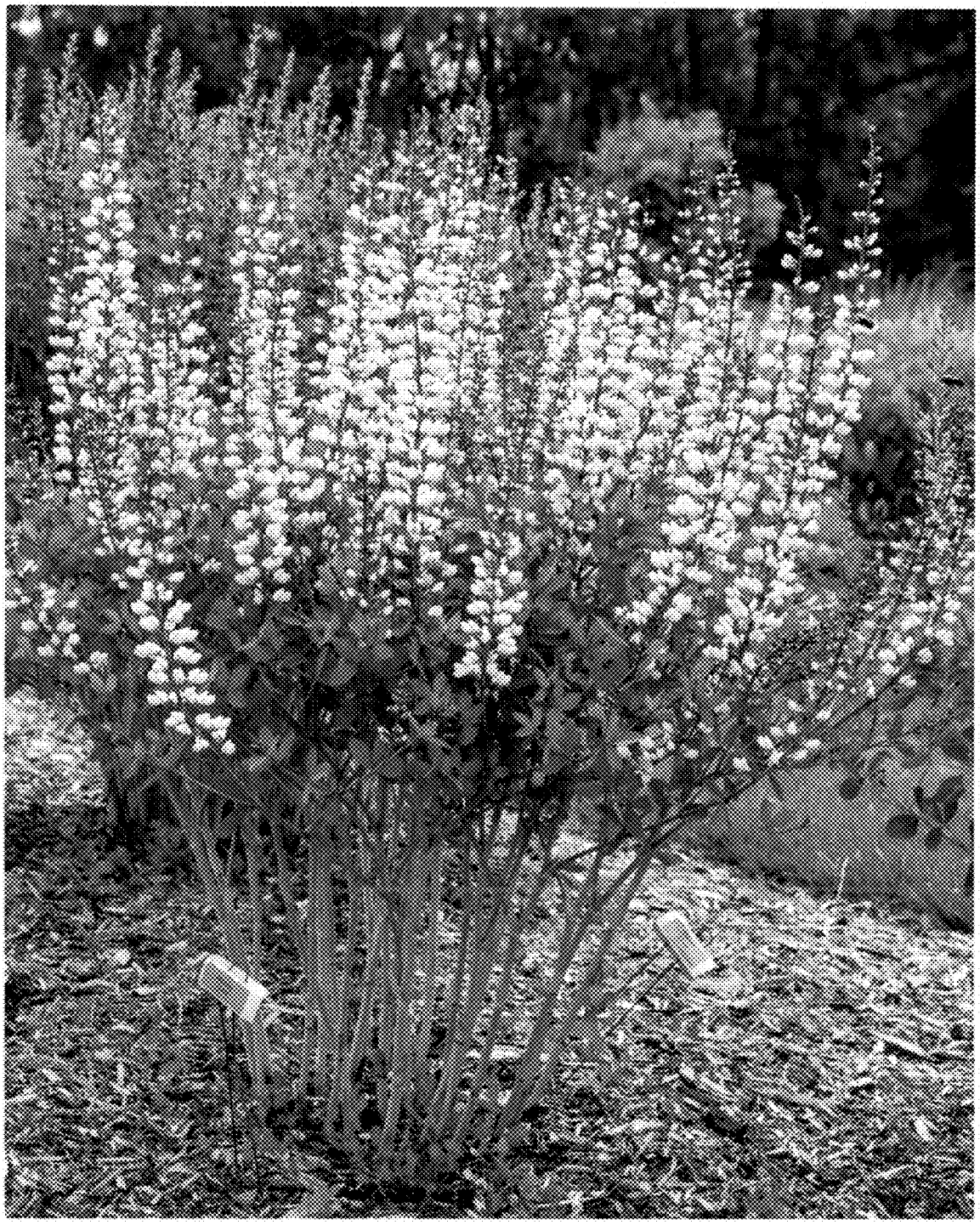
FIG. 1 shows the habit of a plant in full flower.
Figure 2:
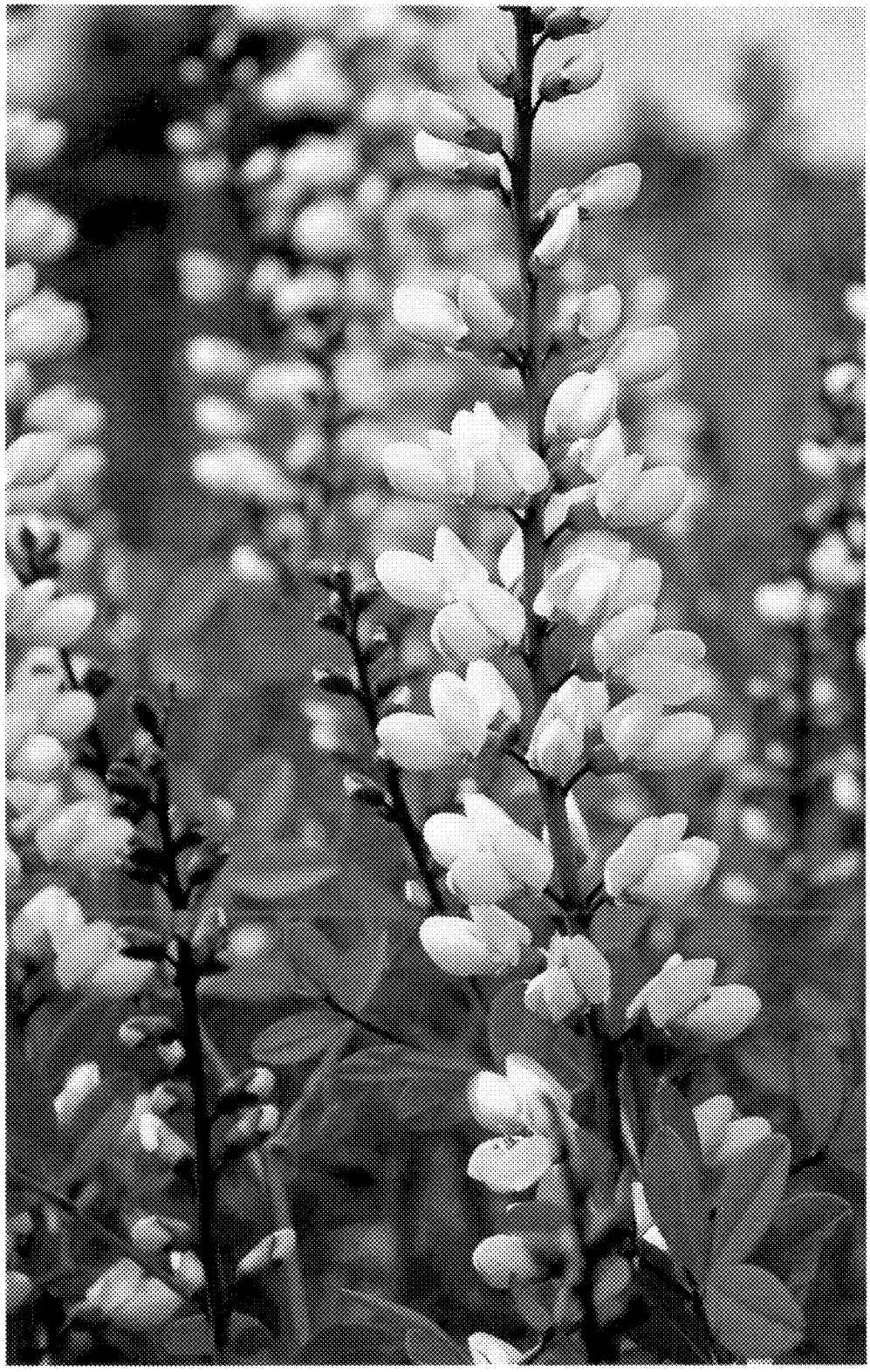
FIG. 2 shows a close-up of the inflorescence with flowers, buds and stems.

The following is a detailed description of a six-year-old plant of the new cultivar as grown outdoors in a display garden at a wholesale perennial nursery in Zeeland, Michigan. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, rounded growth habit with long inflorescences held above the foliage;

Plant size: Stems and crown about 43 cm across at soil level, at flowering to about 137 cm tall from soil to top of flowers and 120 cm wide just below initial flowers; at maturity plant foliage height would be about 103 cm tall and about 130 cm wide;

Roots: Fibrous, well-branched, long, deeply rooted;

Root color: Nearest RHS 161D;

Propagation method: Stem cuttings, rooting in about three weeks;

Growth rate: Moderate to slow;

Stems: Rigid and upright; highly glaucous; glabrous; cylindrical with shallow longitudinal furrows; lower two to three nodes without leaves or branches; normally two to three branches per plant below main peduncle; main stem to about 13 mm diameter at base and 137 cm tall to top of inflorescence, average about 128 cm long and about 9 mm diameter;

Stem color: Between RHS 138B and RHS 147C;

Stem scales: Lanceolate; at stem nodes; dehiscing to leave behind thin scar on stem; about 20 mm wide at base, 25 mm wide in center, about 52 mm long, and 2 mm wide in center of retuse apex with sharply pointed sides; truncate clasping base;

Stem scale color: Between RHS 145C and RHS 147D proximally and strongly blushed with nearest RHS N187A distally before dehiscing;

Branches: Glaucous; glabrous; cylindrical; slightly furrowed; normally about four alternate, primary branches at 50 to 60 degree angle above horizontal; up to 79 cm long and 6 mm diameter, average for primary branches about 45 cm long and 5 mm diameter, smaller distally; and typically three alternate secondary branches per stem of about 47 cm long and 4 mm diameter, averaging about 30 cm long and 3.5 mm diameter; normally two alternate tertiary branches up to 32 cm long and 2 mm diameter, average about 15 cm long and 1.5 mm diameter;

Nodes: Up to 12 cm apart between lowest branches, average about 8.8 cm below main peduncle flowers;

Node color: Nearest RHS 202A;

Foliage: Alternate on stem; ternate to palmately compound with three leaflets; outer two leaflets independent, projecting at slightly less than 90-degree angle to middle leaflet; to about 5 cm long and 9 cm wide;

Leaflet: Three; obovate; apex acute, base cuneate; margins entire; petiolate; adaxial and abaxial surfaces matte and glabrous; slightly glaucous adaxial and glaucous abaxial; middle lobe to about 4.8 cm long and 2.5 cm wide, side lobes to about 4.5 cm long and 2.3 cm wide;

Leaflet color: Newly expanding adaxial and abaxial marginal 0.2 mm nearest RHS N186A and interior between RHS 146D and RHS 146C; mature adaxial nearest RHS 137B and mature abaxial between RHS N138B and RHS 137B;

Venation: Pinnate; glabrous; thin;

Vein color: Newly expanding adaxial midrib between RHS NN137B and RHS N186A, and abaxial midrib nearest RHS N186A, primary veins adaxial and abaxial between RHS 146D and RHS 146C; mature adaxial midrib and primary veins nearest RHS 147C, and abaxial midrib and primary veins between RHS 146D or RHS 145C; secondary veins same color as surrounding leaf tissue;

Petioles: Glabrous; slightly glaucous; concaved facing upward; to about 6 mm long and 1 mm wide, average 3 cm long and 1 mm wide;

Petiole color: On expanding leaves nearest N186A both adaxial and abaxial, on mature leaves both adaxial and abaxial nearest RHS 146C with slight blush around margins of nearest RHS N186A;

Stipules: Narrowly lanceolate, acute apex with base truncate to stem; to about 27 mm long and 12 mm wide, average 21 mm long and 10 mm wide with largest stipules below primary branches and decreasing distally and on secondary branches;

Stipule color: Nearest RHS N138B both surfaces;

Peduncle: Rounded with vertical shallow ridges and furrows; glaucous; glabrous; from first flower to apex about 71 cm long; diameter at the base of first flower about 6 mm and about 2 mm diameter at the apex;

Peduncle color: Nearest RHS N186A on young flowering portions and on mature;

Pedicel: Cylindrical, glabrous, glaucous; about 6 mm long and 1 mm diameter;

Pedicel color: Nearest RHS 146C ventrally and between RHS 146C and RHS N186B dorsally;

Calyx: Campanulate; four-lobed; 10 mm long, 8 mm tall and 8 mm across at apex;

Sepals: Four; one dorsal rarely emarginate with a 1 mm deep notch; one ventral; and two lower lateral; acute apices; fused into tube in proximal 6 mm; margin entire; glabrous adaxial and abaxial; dorsal sepal 10 mm long and 4 mm wide at fusion; other three sepals 8 mm long and 3 mm across at fusion;

Sepal color: Adaxial nearest RHS 147C with a slight blush of nearest RHS N186B; abaxial between RHS 147B and RHS 147C with slight blush of nearest RHS N186B;

Buds one day prior to anthesis: Oblong elliptic, flatted vertically; about 24 mm long and 9 mm tall and 6 mm wide;

Bud color: One day prior to opening exposed keel petal nearest RHS 4D proximally and distally nearest RHS 4C, enfolded banner petal between RHS 4D and RHS 4C with the basal portion nearest RHS 145C, exposed alae petals between RHS 4D and RHS 4C;

Flower: Zygomorphic, papilionaceous, non-secund, held at about 45-degree angle above horizontal; about 75 to 95 flowers per main raceme and about 15 to 42 per secondary branch; seasonally effective for about 3 weeks beginning in late May in Zeeland, MI; individual flower remaining effective and on raceme for about four days;

Flower size: About 26 mm long, 14 mm tall and 8 mm wide at largest portions; consisting of an upper banner, a lower keel made up of two lobes folded around gynoecium and androecium; and two lateral wings or alae laterally appressed against keel;

Flower fragrance: None detected;

Petals: Five; with a lower fused keel, an upper banner, and two lateral wings or alae; keel comprised of two sections that are folded around stamens and pistil;

*Banner petal*.—Longitudinally conduplicate to laterally enrolled; curved upward and backward and concaved in the middle; apex rounded and retuse with 1 mm deep notch; base claw-like; margin entire; about 17 mm long, 8 mm across natural width, 17 mm wide flattened spread, and 6 mm tall; claw about 5 mm long and 1.5 mm wide at base.

*Banner color*.—Adaxial blade center between RHS 145D and RHS 150D, margins between RHS 8D and RHS 11D, lightly maculate with dots of about 0.1 mm diameter or smaller nearest RHS N92A in the center 3 mm diameter, adaxial claw base between RHS 145D and RHS 150D; abaxial blade center between RHS 145D and RHS 150D, margins between RHS 8D and RHS 11D, and lightly maculate with dots of about 0.1 mm diameter or smaller nearest RHS N92A concentrated about 3 to 5 mm from the center, adaxial claw base between RHS 145D and RHS 150D.

*Keel*.—Comprised of two main lobes that are folded around stamens and pistil; fused in the distal one-third with the apex emarginate or retuse and the bases separate and claw-like; margin entire; top edge about one-third of the way from base has 2 mm smaller lobe pointing toward base; about 21 mm long and 8 mm tall, blade portion to about 14 mm long and 8 mm tall, with claw to about 7 mm long and base narrowed to 1 mm wide for the proximal 5 mm.

*Keel color*.—Adaxial and abaxial claw between RHS 145D and RHS 150D; adaxial and abaxial blades between RHS 8D and RHS 11D; remaining unchanged with maturity.

*Alae*.—Two; papilionaceous corolla appendage with rounded apex and claw-like base; with 2.0 mm lobe pointing toward base and about one-third of the way from base; about 21 mm long and 7 mm tall with the claw narrowed to 2 mm wide for the distal 6 mm.

*Alae color*.—Adaxial and abaxial claw between RHS 145D and RHS 150D; adaxial and abaxial main blade portion and small lobe between RHS 8D and RHS 11D; Petal colors remaining unchanged with maturity.

Receptacle: Disk-shaped, about 4 mm diameter and 1.2 mm depth; color nearest RHS NN137B;

Gynoecium: One, with superior ovary and stipe;

*Pistil*.—About 22 mm long and 1.5 mm wide.

*Style*.—Tapered and curved upwardly distally, about 9 mm long and about 0.5 mm diameter above ovary; color nearest RHS 145D.

*Stigma*.—About 0.2 mm diameter; color nearest RHS 145D.

*Ovary*.—Superior above hypanthium, suspended by stipe; about 7 mm long and about 1.5 mm in diameter; color nearest RHS 147A with a slight blush of RHS N186A.

*Stipe*.—About 4 mm long and 0.7 mm diameter; color nearest RHS NN137B with a slight blush nearest RHS N186A.

Androecium:

*Stamens*.—Ten.

*Filament*.—Glabrous; slightly lustrous; not united 20.0 mm in length and about 0.7 mm in diameter; slightly curved upward distally; color nearest RHS 145D.

*Anther*.—Dorsifixed, oblong; about 1.5 mm long and 1 mm wide; color nearest RHS 94B.

*Pollen*.—Spherical; abundant; color nearest RHS 17A.

Fruit: Bivalve inflated pod; glabrous; about 21 mm long, 13 mm across and 14 mm thick; with thin, linear, arcuate, terminal beak to about 11 mm long and about 1 mm thick;

Fruit color.—As maturing a blend between RHS NN137B and RHS N186A, at maturity nearest 199D;

Seeds: About 6 to 14 per flower (open pollinated); reniform; glabrous; about 4 mm long, 3 mm across and 2 mm thick; color between RHS N199D and RHS N199C;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct cultivar of *baptisia* plant named 'Vanilla Cream II' as herein described and illustrated.

* * * * *